United States Patent
Frost et al.

(10) Patent No.: US 6,750,049 B1
(45) Date of Patent: Jun. 15, 2004

(54) SYNTHESIS OF 1,2,3,4-TETRAHYDROXYBENZENES AND 1,2,3-TRIHYDROXYBENZENES USING MYO-INOSITOL-1-PHOSPHATE SYNTHASE AND MYO-INOSITOL 2-DEHYDROGENASE

(75) Inventors: John W. Frost, Okemos, MI (US); Chad A. Hansen, East Lansing, MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 09/937,243

(22) PCT Filed: Mar. 16, 2000

(86) PCT No.: PCT/US00/06808

§ 371 (c)(1), (2), (4) Date: May 7, 2002

(87) PCT Pub. No.: WO00/56911

PCT Pub. Date: Sep. 28, 2000

Related U.S. Application Data

(63) Continuation-in-part of application No. 09/274,732, filed on Mar. 23, 1999, now abandoned.

(51) Int. Cl.$^7$ .............. C12P 7/18; C12N 1/20; C12N 9/04; C12N 9/90

(52) U.S. Cl. ............ 435/158; 435/252.3; 435/252.33; 435/252.4; 435/190; 435/233

(58) Field of Search .................... 435/156, 158, 435/252.3, 252.33, 252.4, 190, 233

(56) References Cited

PUBLICATIONS

Posternak , T. The Cyclitols, p. 164, Holden Day, San Francisco, CA 1965.*
Majumder et al. (1997) Biochem Biophys Acta 1348:245–256.*
Nelson et al. (1998) Plant Cell 10:753–764.*

* cited by examiner

*Primary Examiner*—Rebecca E. Prouty
*Assistant Examiner*—David J Steadman
(74) *Attorney, Agent, or Firm*—Harness, Dickey & Pierce, P.L.C.

(57) ABSTRACT

A bioengineered synthesis scheme for the production of 1,2,3,4-tetrahydroxybenzene from a carbon source is provided. Methods of producing 1,2,3,4-tetrahydroxybenzene from a carbon source based on the synthesis scheme are also provided. Methods are also provided for converting 1,2,3,4-tetrahydroxybenzene to 1,2,3-trihydroxybenzene by catalytic hydrogenation.

41 Claims, 4 Drawing Sheets

<sup>a</sup>Key: (a) phosphoenolpyruvate:carbohydrate phosphotransferase; (b) *myo*-inositol 1-phosphate synthase; (c) phosphatase activity; (d) dehydrogenase activity; (e) 0.5 M $H_2SO_4$, $H_2O$, reflux.

aKey: (a) Cl₂C(O), pyridine, xylene, reflux; (b) H₂SO₄, HNO₃; (c) KOH (aq.); (d) Zn, HCl; (e) H₂O, reflux; (f) BnBr, K₂CO₃, acetone, reflux, 83 %; (g) K₃Fe(CN)₆, H₂O₂, AcOH, 11 %; (h) H₂, 10 %Pd/C, EtOH, 100 %; (i) N-methylformanilide, POCl₃, 60 °C, 93 %; (j) HCO₂H, H₂O₂, CH₂Cl₂, 0 °C to rt, 95 %; (k) H₂, 10 % Pd/C, EtOH, 80%.

$^a$Key: (a) $(CH_3)_2SO_4$, NaOH, 69 %; (b) (i) n-BuLi, TMEDA, hexanes, THF, 0 °C; (ii) $CH_3I$, 0 °C, 83%; (c) (i) n-BuLi, TMEDA, hexanes, 0 °C; (ii) CuCN, THF, $Et_2O$, 0 °C; (iii) farnesyl bromide, -78 °C, 57 %; (d) CAN, pyridine-2,6-dicarboxylate, $CH_3CN/H_2O$, 0 °C, 46%.

SYNTHESIS OF 1,2,3,4-TETRAHYDROXYBENZENES AND 1,2,3-TRIHYDROXYBENZENES USING MYO-INOSITOL-1-PHOSPHATE SYNTHASE AND MYO-INOSITOL 2-DEHYDROGENASE

RELATED APPLICATIONS

The present invention is a continuation-in-part of U.S. Ser. No. 09/274,732, filed Mar. 23, 1999, now abandoned which is hereby expressly incorporated by reference.

SPONSORSHIP

Work on this invention was sponsored in part by the National Science Foundation Grant No. CHE963368. The Government may have certain rights in the invention.

FIELD OF THE INVENTION

The present invention is related to the production of 1,2,3,4-tetrahydroxybenzene and more specifically, to methods of producing 1,2,3,4-tetrahydroxybenzene from the bioconversion of a carbon source.

BACKGROUND OF THE INVENTION

Polyhydroxy benzenes and quinones possessing the oxygenation pattern of 1,2,3,4-tetrahydroxybenzene 1 (FIG. 1) often display biological activity. Aurantiogliocladin 2 and fumigatin 3 (FIG. 1) are antibiotics. Vischer, E. B., *J. Chem. Soc.* 815 (1953): Baker, W. et al., *J. Chem. Soc.* 820 (1953); Baker, W. et al., *J. Chem. Soc.* 670 (1941). Coenzyme $Q_{n=10}$4 (FIG. 1) is an essential antioxidant in humans protecting low density lipoproteins from atherosclerosis-related oxidative modification. Ingold, K. U. et al., *PNAS (USA)* 90:45 (1993); Stocker, R. et al., *PNAS (USA)* 88:1646 (1991) Steinberg, D., *Circulation* 84:1420 (1991). Dillapiole 5 (FIG. 1) is a pyrethrin synergist and is responsible for the sedative effect of *Perilla frutescens* leaves. Honda, G. et al., *Chem. Pharm. Bull.* 36:3153 (1988): Tomar, S. S. et al., *Agric. Biol. Chem.* 50:2115 (1986).

The current method of preparing 1,2,3,4-tetrahydroxybenzene uses pyrogallol as the synthetic starting material. Pyrogallol is converted to aminopyrogallol using a four-step synthesis. Aminopyrogallol is then hydrolyzed to give 1,2,3,4-tetrahydroxybenzene. Conversion of pyrogallol to 1,2,3,4-tetrahydroxybenzene requires the use of such reagents as phosgene, solvents such as pyridine and xylene, and has a nitroaromatic as a synthetic intermediate.

It would also be desirable to provide an improved method for producing derivatives of 1,2,3,4-tetrahydroxybenzene. Particularly, it would be desirable to provide a method for producing 1,2,3-trihydroxybenzene (pyrogallol). It would also be desirable if such a method were cost efficient and employed readily available materials. Currently, 1,2,3-trihydroxybenzene is obtained by thermal decarboxylation of gallic acid. However, gallic acid is isolated from natural sources such as gall nuts and tara powder and therefore is in limited supply.

It would thus be desirable to provide an improved method for producing 1,2,3,4-tetrahydroxybenzene. It would also be desirable if such a method was cost-efficient, using inexpensive starting materials. It would be further desirable if the method employed non-toxic compounds and was environmentally benign.

SUMMARY OF THE INVENTION

A bioengineered synthesis scheme for the production of 1,2,3,4-tetrahydroxybenzene from a carbon source is provided. In one embodiment, the bioconversion methods of the present invention comprise the steps of microbe-catalyzed conversion of a carbon source to myo-2-inosose followed by acid-catalyzed dehydration of myo-2-inosose to produce 1,2,3,4-tetrahydroxybenzene. As shown in the synthesis scheme of FIG. 2, the microbe-catalyzed conversion step of the present invention requires four enzymes. In one embodiment, the microbe-catalyzed conversion comprises the conversion of a carbon source to myo-inositol by a recombinant microbe and the subsequent conversion of myo-inositol to myo-2-inosose catalyzed by a second microbe. In another embodiment, the recombinant microbe is *Escherichia coli* designed to cause the conversion of glucose-6-phosphate to myo-inositol-1-phosphate. In yet another embodiment, the conversion of myo-inositol to myo-2-inosose is catalyzed by the microbe *Gluconobacter oxydans*. Acid-catalyzed dehydration of the resulting myo-2-inosose yields 1,2,3,4-tetrahydroxybenzene.

The biocatalytic synthesis of 1,2,3,4-tetrahydroxybenzene provided herein is environmentally benign, economically attractive, and utilizes abundant renewable sources as a starting material.

Methods are also provided for the production of derivatives of 1,2,3,4-tetrahydroxybenzene, particularly Coenzyme Q 1,2,3-trihydroxybenzene (pyrogallol). In one embodiment 1,2,3-trihydroxybenzene is produced by reduction of 1,2,3,4-tetrahydroxybenzene. In a preferred embodiment, the reduction is achieved by catalytic hydrogenation followed by hydrolysis.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

Figure 1:
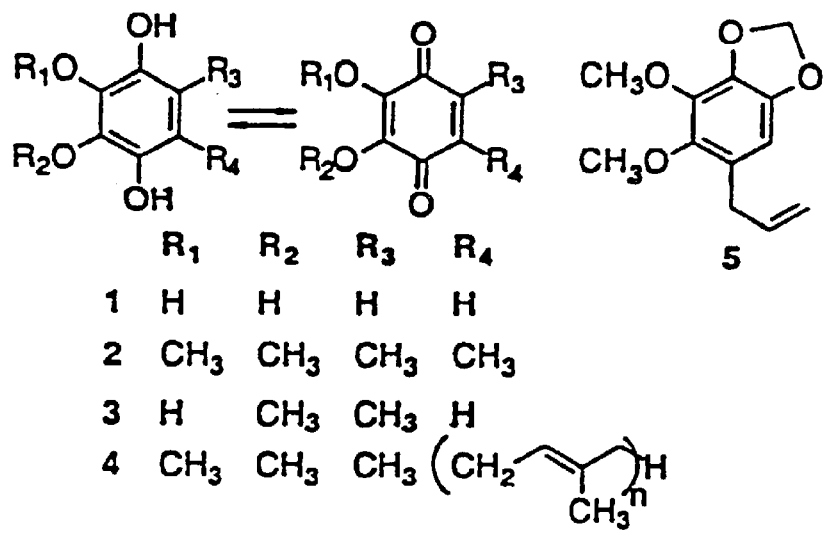
FIG. 1 is an illustration showing the structures of products that can be derived from 1,2,3,4-tetrahydroxybenzene.

A bioengineered synthesis scheme for the production of 1,2,3,4-tetrahydroxybenzene from a carbon source is provided herein. Methods of producing 1,2,3,4-tetrahydroxybenzene from a carbon source based on the synthesis scheme are also provided. In one embodiment, a method is provided wherein the carbon source is converted to myo-inositol by a recombinant microbe, the myo-inositol is further converted to myo-2-inosose by a second microbe, followed by acid-catalyzed dehydration of myo-2-inosose to produce 1,2,3,4-tetrahydroxybenzene.

Novel methods are also provided for the production of derivatives of 1,2,3,4-tetrahydroxybenzene, particularly 1,2,3-trihydroxybenzene (pyrogallol). In one embodiment 1,2,3-trihydroxybenzene is produced by reduction of 1,2,3,4-tetrahydroxybenzene. In a preferred embodiment, the reduction is achieved by catalytic hydrogenation of 1,2,3,4-tetrahydroxybenzene followed by acid catalyzed hydrolysis to yield 1,2,3-trihydroxybenzene. In a more preferred embodiment, the hydrogenation is catalyzed by $Rh/Al_2O_3$. These methods take advantage of inexpensive and abundant carbon sources as starting materials to produce 1,2,3,4-tetrahydroxybenzene which can then be converted to 1,2,3-trihydroxybenzene.

Although microbe-catalyzed conversion of a carbon source to myo-inositol by a recombinant microbe followed by conversion of the myo-inositol to myo-2-inosose by a second microbe is described in detail herein, in an alternative embodiment, a single recombinant microbe is employed to convert a carbon source directly to myo-2-inosose which is then converted to 1,2,3,4-tetrahydroxybenzene by an acid-catalyzed dehydration. This single-microbe conversion may be carried out by any type of microbe sufficiently engineered to produce the desired outcome.

In another alternative embodiment, a recombinant microbe catalyzes the conversion of a carbon source to D-2,3-diketo-4-deoxy-epi-inositol which is subsequently converted to 1,2,3,4-tetrahydroxybenzene by an acid-catalyzed dehydration. D-2,3-Diketo-4-deoxy-epi-inositol is an intermediate in the microbial catabolism of myo-inositol as well as a likely intermediate in the acid-catalyzed conversion of myo-2-inosose into 1,2,3,4-tetrahydroxybenzene.

The bioconversion methods of the present invention are carried out under conditions of time, temperature, pH, nutrient type and concentration, aeration conditions and glucose concentrations, to provide maximal conversion of the carbon source to 1,2,3,4-tetrahydroxybenzene. As described in detail in Specific Example 1, in a preferred embodiment, a fed-batch fermentor is used to convert the carbon source to myo-inositol, followed by isolation of myo-inositol, e.g., deionization and decolorization of the fermentation broth and precipitation by the addition of an organic solvent. The isolated myo-inositol is then converted to myo-inositol to myo-2-inosose followed by isolation of the myo-2-inosose, e.g., precipitation of the myo-2-inosose from the culture broth. The fed-batch fermentor process and the precipitation methods are also known to those skilled in the art.

As used herein, the phrase "carbon source" is meant to include biomass-derived carbon sources including, but not limited to, xylose, arabinose, glycerol, glucose and the intermediates (e.g., dicarboxylic acids) in the Krebs cycle, either alone or in combination. In a preferred embodiment, the carbon source is glucose.

In one embodiment, a recombinant E. coli microbe is employed in the methods of the present invention. In a preferred embodiment, the E. coli comprises a nonfunctional serA locus. This recombinant E. coli, designated, JWF1, may further comprise a plasmid carrying an INO1 gene insert and a serA gene insert. The INO1 gene encodes myo-inositol-1-phosphate synthase which converts glucose-6-phosphate to myo-inositol-1-phosphate. In a preferred embodiment, the INO1 gene is from *Saccharomyces cerevisiae*. Overexpression of myo-inositol-1-phosphate synthase will increase carbon flow into the myo-inositol pathway. This recombinant microbe is capable of converting glucose to myo-inositol.

In another embodiment, the myo-inositol produced by the first recombinant microbe, is converted to myo-2-inosose by a second microbe. This second microbe can either be a recombinant microbe or a naturally occurring microbe. A recombinant microbe comprises a plasmid carrying the iolG gene insert. The iolG gene insert encodes the enzyme inositol dehydrogenase, which catalyzes the conversion of myo-inositol to myo-2-inosose. Alternatively, the iolG gene insert is inserted directly into the genome of the recombinant microbe. Preferably, the iolG gene is isolated from *Bacillus subtilis*. In a preferred embodiment, the second microbe is a naturally occurring microbe that express inositol dehydrogenase activity. Examples of such microbes include, but are not limited to, *Bacillus subtilis* and *Gluconobacter oxydans*. In a preferred embodiment, the second microbe is *G. oxydans*, which converts myo-inositol to myo-2-inosose without loss of the myo-2-inosose product to further catabolism.

In a preferred embodiment, the recombinant E. coli comprises plasmid pAD1.88A carrying an INO1 gene insert and a serA gene insert. As described above, the INO1 gene insert encodes myo-inositol-1-phosphate synthase which converts glucose-6-phosphate to myo-inositol-1-phosphate, thus increasing the carbon flow into the myo-inositol pathway. Due to a mutation in the E. coli genomic serA locus required for L-serine biosynthesis, growth in minimal salts medium and plasmid maintenance follows from expression of plasmid-localized serA. The serA insert thus allows microbial growth in minimal salts medium, distinguishing the microbes containing the plasmid from non-plasmid containing microbes.

In an alternative embodiment, the recombinant E. coli comprises a plasmid carrying an INO1 gene insert, an iolG gene insert and a serA gene insert. As described above, the iolG gene insert encodes inositol dehydrogenase which catalyzes the conversion of myo-inositol to myo-2-inosose. In a preferred embodiment, the plasmid also carries the gene insert for inositol monophosphatase. While not wishing to be bound by theory, hydrolysis of myo-inositol-1-phosphate to produce myo-inositol can occur in the cytosol or periplasm. If a cytoplasmic phosphatase hydrolyzes myo-inositol-1-phosphate, plasmid-localized INO1 and iolG will lead to myo-2-inosose synthesis. Periplasmic phosphatase activity would result in periplasmic production of myo-inositol while inositol dehydrogenase expression is localized in the cytoplasm. Transport of myo-inositol from the periplasm into the cytoplasm is unlikely in E. coli given that this microbe does not catabolize myo-inositol. To correct for periplasmic phosphatase activity, plasmid-localization of genes encoding mammalian inositol monophosphatase, which have been cloned, sequenced, and successfully expressed in E. coli, would be desirable. Diehl, R. E. et al., J. Biol. Chem. 265:5946 (11990); McAllister, G. et al., Biochem. J. 284:749 (1992). Because of the specificity of this enzyme for myo-inositol-1-phosphate, a molecule which is not a normal metabolite in E. coli, cytoplasmic expression of the cDNA encoding inositol monophosphatase in E. coli should not be problematic. An E. coli comprising a plasmid carrying both the INO1 gene insert and the iolG gene insert and the gene for inositol monophosphatase can convert glucose directly to myo-2-inosose. The myo-2-inosose can then be converted to 1,2,3,4-tetrahydroxybenzene by an acid-catalyzed dehydration.

In another embodiment, the recombinant E. coli, designated JWF1, comprises a plasmid carrying an INO1 gene insert, an iolG gene insert, and a serA gene insert. This recombinant microbe is capable of converting glucose to myo-2-inosose. In a preferred embodiment, the recombinant *E. coli* comprises plasmid pAD2.28A carrying an INO1 gene insert, an iolG gene insert and a serA gene insert. Examples of these recombinant microbes, *E. coli* JWF1/pAD1.88A and JWF1/pAD2.28A, are described in Specific Examples 1 and 4, respectively, and have been deposited with the American Type Culture Collection (ATCC), 10801 University Boulevard, Manassas, Va. 20110-2209, under the terms of the Budapest Treaty, and accorded the ATCC designation numbers 207153 and 207154, respectively. The deposit will be maintained in the ATCC depository, which is a public depository, for a period of 30 years, or 5 years after the most recent request, or for the effective life of a patent, whichever is longer, and will be replaced if the deposit becomes depleted or non-viable during that period. Samples of the deposit will become available to the public and all restrictions imposed on access to the deposit will be removed upon grant of a patent on this application.

In yet another embodiment, a recombinant *E. coli* is employed to convert glucose to D-2,3-diketo-4-deoxy-epi-inositol. Such a recombinant *E. coli* comprises a plasmid carrying the INO1 gene insert, the iolG gene insert and the gene insert encoding for the enzyme, myo-2-inosose dehydratase. The plasmid may further comprise the gene insert for inositol monophosphatase. Myo-2-inosose dehydratase catalyzes the conversion of myo-2-inosose to D-2,3-diketo-4-deoxy-epi-inositol which can undergo an acid-catalyzed dehydration to yield 1,2,3,4-tetrahydroxybenzene. While not wishing to be bound by theory, D-2,3-diketo-4-deoxy-epi-inositol is likely the first intermediate in the acid-catalyzed conversion of myo-2-inosose to 1,2,3,4-tetrahydroxybenzene. Acid-catalyzed aromatization of D-2,3-diketo-4-deoxy-epi-inositol would eliminate a step and may lead to higher yields of 1,2,3,4-tetrahydroxybenzene as compared to the acid-catalyzed dehydration of myo-2-inosose.

It will be appreciated that the INO1 gene, iolG gene, serA gene and the genes encoding inositol dehydrogenase, inositol monophosphatase and/or myo-2-inosose dehydratase, can be inserted directly into the *E. coli* genome. Such a recombinant *E. coli* would not require a plasmid to produce significant amounts of myo-inositol, myo-2-inosose or D-2,3-diketo-4-deoxy-epi-inositol.

Although *E. coli* is specifically described herein as the microbe for carrying out the methods of the present invention, it will be appreciated that any microorganism such as the common types cited in the literature and known to those skilled in the art, may be employed, provided the microorganism can be altered to effect the desired conversion (e.g., carbon source to myo-inositol, carbon source to myo-2-inosose, carbon source to D-2,3-diketo-4-deoxy-epi-inositol, myo-inositol to myo-2-inosose, etc.). Thus it is envisaged that many types of fungi, bacteria and yeasts will work in the methods of the present invention. Such microorganisms may be developed, for example, through selection, mutation, and/or genetic transformation processes with the characteristic and necessary capability of converting one constituent of the synthesis scheme of the present invention to another. Methods for such development are well known to the skilled practitioner.

In order to carry out the bioconversion methods of the present invention, a solution containing a carbon source is contacted with the recombinant or wild-type microbe to form a bioconversion mixture which is maintained under appropriate conditions to promote the conversion of the carbon source to the desired constituent, e.g., myo-inositol or myo-2-inosose. In a preferred embodiment, the bioconversion mixture is maintained at a temperature of about 30° C. to about 37° C. and a pH of about 6.5 to about 7.5. It is preferred that the bioconversion mixture also contain other substances necessary to promote viability of the microbes such as mineral salts, buffers, cofactors, nutrient substances and the like. The more general requirements for the maintenance of viability of microorganisms are well known and specific requirements for maintaining the viability of specific organisms are also well known as documented in the literature, or are otherwise easily determined by those skilled in the art.

In another embodiment, the myo-inositol produced in the fermentation broth of the first bioconversion with the first microbe can be isolated before being utilized in the second bioconversion. The isolation can be a total isolation to provide pure myo-inositol as described in Specific Example 1. The isolation can also be a partial isolation where the fermentation broth is deproteinized and decolorized before use in the second bioconversion. Such deproteinization and decolorization are well known to those skilled in the art. Further purification of the myo-inositol can be obtained by concentration of the deproteinized/decolorized fermentation broth to a volume where the myo-inositol concentration is greater than 50 g/L. At concentrations greater than 50 g/L, the myo-inositol can be precipitated out by the addition of methanol. By way of non-limiting example, myo-inositol can be isolated from the fermentation broth by the following four steps: ultrafiltration to remove cells and proteins; decolorization by activated charcoal; concentration of the fermentation broth to give a myo-inositol concentration greater than 50 g/L; and precipitation of myo-inositol by the addition of methanol. The myo-inositol precipitate can be washed, resuspended in buffer or water, and used in the second bioconversion to myo-2-inosose.

Novel methods for converting 1,2,3,4-tetrahydroxybenzene to 1,2,3-trihydroxybenzene are also provided. In one embodiment, a method is provided wherein 1,2,3,4-tetrahydroxybenzene is reduced to 1,2,3-trihydroxybenzene.

In one embodiment, the 1,2,3,4-tetrahydroxybenzene is converted to 1,2,3-trihydroxybenzene by hydrogenation in the presence of a catalyst followed by acid catalyzed hydrolysis. In a preferred embodiment, the catalyst is $Rh/Al_2O_3$. The amount of catalyst required and the conditions required for hydrogenation (e.g., pressure, time) are well known to the skilled practitioner.

In another embodiment, the hydrogenation reaction is carried out in an aqueous 1,2,3,4-tetrahydroxybenzene solution. In a preferred embodiment, the aqueous 1,2,3,4-tetrahydroxybenzene solution will be free of any compounds known to quench the hydrogenolysis catalyst. In a more preferred embodiment, the aqueous 1,2,3,4-tetrahydroxybenzene solution is comprised of isolated 1,2,3,4-tetrahydroxybenzene and water.

In order to more fully demonstrate the advantages arising from the present invention, the following examples are set forth. It is to be understood that the following is by way of example only and is not intended as a limitation on the scope of the invention.

SPECIFIC EXAMPLE 1

Synthesis of 1,2,3,4-Tetrahydroxybenzene from Glucose

I. Results

Figure 2:
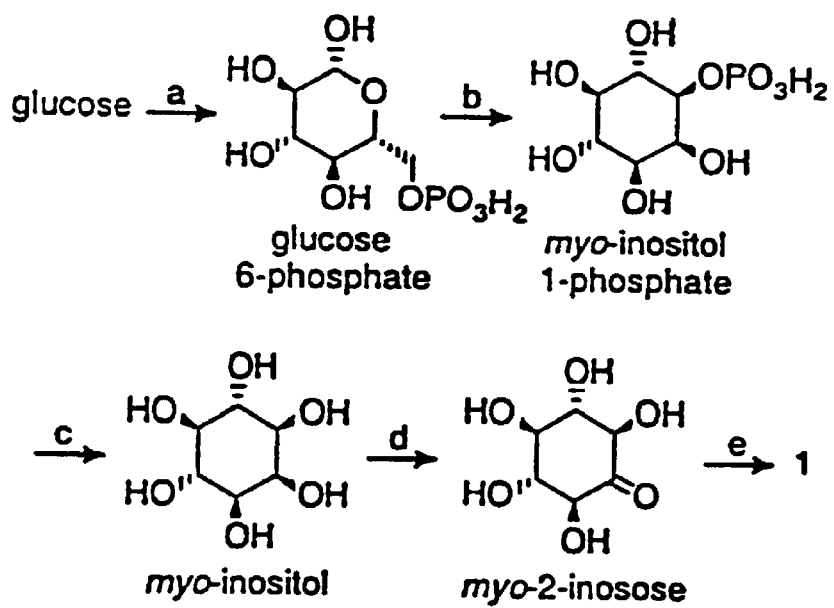
FIG. 2 is a schematic illustrating the bioengineered synthesis scheme of the present invention for producing 1,2,3,4-tetrahydroxybenzene.

A synthetic route (FIG. 2) has now been elaborated which provides convenient access to 1,2,3,4-tetrahydroxybenzene via myo-inositol intermediacy. The general utility of this route is demonstrated by a concise synthesis of coenzyme $Q_{n=3}$4. While the shikimate pathway and polyketide biosynthesis have traditionally provided biocatalytic access to aromatic chemicals, syntheses of 1,2,3,4-tetrahydroxybenzene 1 and coenzyme $Q_{n=3}$4 are distinguished by the recruitment of myo-inositol biosynthesis.

Synthesis of myo-inositol by *E. coli* JWF1/pAD1.88A begins with D-glucose uptake and conversion to D-glucose-6-phosphate catalyzed by the *E. coli* phosphotransferase system (Postma, P. W. et al., In *Escherichia coli* and *Salmonella*, 2nd ed., Neidhardt, F. C. et al., Eds., ASM: Washington, Vol. 1, p. 1149 (1996)) where phosphoenolpyruvate is the source of the transferred phosphoryl group. D-Glucose-6-phosphate then undergoes cyclization to myo-inositol 1-phosphate catalyzed by myo-inositol-1-phosphate synthase. This enzyme activity, which results from expression of the *Saccharomyces cerevisiae* INO1 gene (Dean-Johnson, M. et al., *J. Biol. Chem.* 264:1274 11989)) on plasmid pAD1.88A, varied significantly (0.022, 0.043, 0.018, and 0.009 μmol/min/mg at 18 h, 30 h, 42 h, and 54 h, respectively) over the course of the fermentation.

Figure 3:
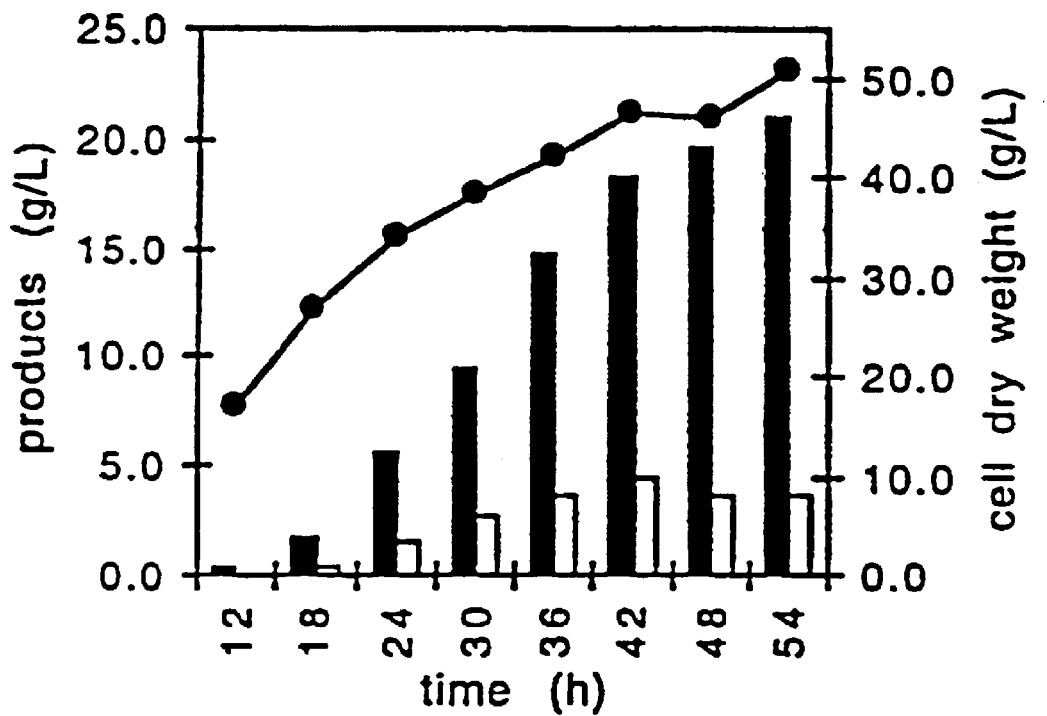
FIG. 3 is a graph showing the production of myo-inositol (solid bars) and myo-inositol-1-phosphate (open bars) in comparison to cell dry weight (filled circles).

*E. coli* JWF1/pAD1.88A synthesized 21 g/L myo-inositol (solid bars, FIG. 3) and 4 g/L myo-inositol-1-phosphate (open bars, FIG. 3) in 11% combined yield (mol/mol) from D-glucose under fed-batch fermentor conditions. Both myo-inositol and myo-inositol-1-phosphate accumulated in the culture supernatant. In eucaryotes, hydrolysis of myo-inositol-1-phosphate to myo-inositol is catalyzed by the enzyme inositol monophosphatase. McAllister, G. et al., *Biochem. J.* 284:749 (1992). Phosphoester hydrolysis was fortuitously catalyzed in *E. coli* JWF1/pAD1.88A by unidentified cytosolic or periplasmic phosphatase activity.

Oxidation of myo-inositol to myo-2-inosose, the next step in the conversion of D-glucose into 1,2,3,4-tetrahydroxybenzene 1, is the first catabolic step when myo-inositol is used as a sole source of carbon for growth and metabolism by microbes such as *Bacillus subtilis*. Yoshida, K.-I. et al., *J. Bacteriol.* 179:4591 (1997). myo-Inositol can also be oxidized by *Gluconobacter oxydans* without loss of product myo-2-inosose to catabolism. Posternak, T., *Bioch. Prep.* 2:57 (1952). Accordingly, incubation of *G. oxydans* ATCC 621 in medium containing microbe-synthesized myo-inositol led to the formation of myo-2-inosose (Scheme 1) in 95% isolated yield.

Inososes have been thought to be stable under acidic conditions and reactive under basic conditions with reported aromatizations resulting from successive β-eliminations being dominated by formation of 1,2,3,5-tetrahydroxybenzene. Posternak, T., *The Cyclitols*, Holden-Day: San Francisco, Chap. 8 (1965); Angyal, S. J. et al., *Carbohydr. Res.* 76:121 (1979). However, it was observed that myo-2-inosose was reactive under acidic conditions with no apparent formation of 1,2,3,5-tetrahydroxybenzene. Refluxing *G. oxydans*-produced myo-2-inosose for 9 h in degassed, aqueous 0.5 M $H_2SO_4$ under argon cleanly afforded 1,2,3,4-tetrahydroxybenzene in 66% isolated yield.

II. Materials And Methods

General. $^1$H NMR spectra were recorded on a 300 MHz spectrometer. Chemical shifts for $^1$H NMR spectra are reported (in parts per million) relative to internal tetramethylsilane ($Me_4Si$, δ=0.0 ppm) with $CDCl_3$ as solvent, to sodium 3-(trimethylsilyl)propionate-2,2,3,3-$d_4$ (TSP, δ=0.0 ppm) when $D_2O$ was the solvent, and to acetone ($CHD_2COCD_3$, δ=2.04 ppm) with $d_6$-acetone. $^{13}$C NMR spectra were recorded at 75 MHz. Chemical shifts for $^{13}$C NMR spectra are reported (in parts per million) relative to $CDCl_3$ (δ=77.0 ppm), relative to $CD_3COCD_3$ (δ=29.8 ppm), and relative to internal $CH_3OH$ (δ=49.0 ppm) or internal $CH_3CN$ (δ=1.4 ppm) in $D_2O$. FAB mass spectra were performed by University of South Carolina (Columbia, S. C.). Elemental analyses were performed by Atlantic Microlab Inc. (Norcross, Ga.). Melting points were uncorrected and were determined using a Mel-Temp II melting point apparatus.

Radial chromatography was carried out with a Harrison Associates Chromatotron using 1, 2 or 4 mm layers of silica gel 60 $PF_{254}$ containing gypsum (E. Merck). Silica gel 60(40–63 μm E. Merck) was used for flash chromatography. Analytical thin-layer chromatography (TLC) utilized pre-coated plates of silica gel 60 F-254 (0.25 mm, E. Merck or Whatman). TLC plates were visualized by immersion in anisaldehyde stain (by volume: 93% ethanol, 3.5% sulfuric acid, 1% acetic acid and 2.5% anisaldehyde) followed by heating. Dimethylformamide, N-methylformanilide and acetone were dried and stored over activated Linde 4 Å molecular sieves under Ar. Tetrahydrofuran and diethyl ether were distilled under nitrogen from sodium benzophenone ketyl. n-Hexanes and TMEDA were distilled from sodium under Ar and stored over activated Linde 4 Å molecular sieves under Ar. Organic solutions of products were dried over $MgSO_4$.

For $^1$H NMR quantitation of solute concentrations during microbial synthesis of myo-inositol and myo-2-inosose, solutions were concentrated to dryness under reduced pressure, concentrated to dryness one additional time from $D_2O$, and then redissolved in $D_2O$ containing a known concentration of TSP purchased from Lancaster Synthesis Inc. Concentrations were determined by comparison of integrals corresponding to each compound with the integral corresponding to TSP (δ=0.00 ppm) in the $^1$H NMR. Protein concentrations were determined using the Bradford dye-binding procedure (Bradford, M. M., *Anal. Biochem.* 72:248 (1979)) by comparison with a standard curve prepared with bovine serum albumin. Protein assay solution was purchased from Bio-Rad. *E. coli* DH5α is available from Gibco BRL.

Culture Medium. All culture solutions were prepared in distilled, deionized water. LB medium (1 L) contained Bacto tryptone (10 g), Bacto yeast extract (5 g); and NaCl (10 g). M9 salts (1 L) contained $Na_2HPO_4$ (6 g), $KH_2PO_4$ (3 g), NaCl (0.5 g) and $NH_4Cl$ (1 g). M9 minimal medium (1 L) consisted of 1 L of M9 salts containing D-glucose (10 g), $MgSO_4$ (0.12 g), and thiamine hydrochloride (0.001 g). Ampicillin was added (0.05 g/L) where indicated. Solutions of M9 salts, $MgSO_4$, and glucose were autoclaved individually and then mixed. Ampicillin was sterilized through a 0.22 μm membrane. Solid medium was prepared by addition of 1.5% (w/v) Difco agar to medium.

Fermentation medium (1 L) contained $K_2HPO_4$ (7.5 g), ammonium iron(III) citrate (0.3 g), citric acid monohydrate (2.1 g), and concentrated $H_2SO_4$ (1.2 mL). The fermentation medium was adjusted to pH 7.0 by addition of concentrated $NH_4OH$ before autoclaving. The following supplements were added immediately prior to initiation of the fermentation: D-glucose (20 g), $MgSO_4$ (0.24 g), and trace minerals including $(NH_4)_6(Mo_7O_{24}).4H_2O$(0.0037 g), $ZnSO_4.7H_2O$ (0.0029 g), $H_3BO_3$ (0.0247 g), $CuSO_4.5H_2O$ (0.0025 g), and $MnCl_2.4H_2O$ (0.0158 g). D-Glucose and $MgSO_4$ were autoclaved separately while trace minerals were sterilized through 0.22 μm membranes prior to addition to the medium.

Genetic Manipulations. Standard procedures were used for the construction, purification, and analysis of plasmid DNA. Sambrook, J. et al., Molecular Cloning A Laboratory Manual, Cold Spring Harbor Laboratory Press: New York (1989). *E. coli* DH5α served as the host strain for all plasmid constructions. The INO1 open reading frame was amplified from pJH318 (Hirsch, J. P. et al., *Mol. Cell. Biol.* 6:3.320 (1986)) using PCR. Inclusion of EcoRI recognition sequences facilitated localization of INO1 into the EcoRI site in pJF118EH (Furste, J. P. et al., Gene 48:119 (1986)) to afford pAD1.45A. Transcription of INO1 in pAD1.45A utilized the vector-encoded tac promoter ($P_{tac}$) which was regulated by vector-encoded expression of $lacI^Q$. Digestion of pD2625 with DraI and EcoRV liberated a 1.9 kb serA fragment that was subsequently ligated into the SmaI site of pAD1.45A to provide pAD1.88A.

*E. coli* JWF1 was prepared by homologous recombination of a non-functional serA gene into *E. coli* RB791(W3110 $lacI^Q$). Localization of the 1.9 kb serA fragment obtained from pD2625 into pMAK705 (Hamilton, C. M. et al., *J. Bacteriol.* 171:4617 (1989)) provided pLZ1.68A. Linearization of pLZ1.68A at the unique BamHI site internal to serA followed by treatment with Klenow fragment and dNTP's and relegation afforded pLZ1.71A. Homologous recombination (Ohta, K. et al., *Appl. Environ. Microbiol.* 57:893 (1991)) of the resulting non-functional serA locus of pLZ1.71A into RB791 afforded JWF1.

myo-Inositol-1-phosphate synthase activity. Partial purification of cellular lysate was required to quantify myo-inositol-1-phosphate synthase activity over background cellular phosphatase activity. Cells were collected from 30 mL of fermentation broth by centrifugation at 2000 g for 6 min at 4° C. Cells were resuspended in 10 mL of resuspension buffer consisting of Tris.HCl (20 mM), pH 7.4, $NH_4Cl$ (10 mM), 2-mercaptoethanol (β-ME, 10 mM), phenylmethylsulphonyl fluoride (PMSF, 2 mM), and EDTA (1 mM). Resuspended cells were frozen at −80° C. for up to 4 days until purification was carried out.

Thawed cells were lysed by two passages through a French press at 2000 psi. Cellular debris was removed by centrifugation at 30000 g for 30 min at 4° C. Clarified cellular lysate containing approximately 200 mg of protein was loaded onto a DEAE cellulose column (15×25 cm) at 4° C. The column was eluted with a step gradient of $NH_4Cl$ in the following buffer (Buffer A): Tris.HCl (20 mM), pH 7.4, β-ME (10 mM), PMSF (1 mM), and EDTA (1 mM). The step gradient consisted of 20 mL of Buffer A with $NH_4Cl$ (10 mM), 45 mL of Buffer A with $NH_4Cl$ (90 mM), and 100 mL of Buffer A with $NH_4Cl$ (150 mM). Fractions (9 mL) were collected throughout the step gradient. Fractions 10–18 were collected and concentrated to less than 5 mL using an Amicon Ultrafiltration Stirred Cell equipped with a PM10 membrane. Concentrated protein (1.5–2.0 mg) was used to measure myo-inositol-1-phosphate synthase activity. The myo-inositol-1-phosphate synthase activity was measured as previously reported (Migaud, M. E. et al., *J. Am. Chem. Soc.* 118:495 11996)) except that the assay solution contained Tris.HCl (20 mM), pH 7.4, $NH_4Cl$ (2 mM), and DTT (0.2 mM).

myo-inositol. Fermentations employed a 2.0 L working capacity B. Braun MD2 culture vessel. Utilities were supplied by a B. Braun Biostat MD controlled by a Dell Optiplex $Gs^+5166$ personal computer equipped with B. Braun MFCS/Win software. Temperature, pH, and glucose feeding were controlled with PID control loops. Temperature was maintained at 33° C. pH was maintained at 7.0 by addition of concentrated $NH_4OH$ or 2 N $H_2SO_4$. Dissolved oxygen (D. O.) was measured using a Mettler-Toledo 12 mm sterilizable $O_2$ sensor fitted with an Ingold A-type $O_2$ permeable membrane. D. O. was maintained at 10% air saturation. Antifoam (Sigma 204) was added manually as needed.

Inoculants were started by introduction of a single colony of JWF1/pAD1.88A into 100 mL M9 medium containing ampicillin. The culture was grown at 37° C. with agitation at 250 rpm for 15 h and then transferred to the fermentation vessel. The initial glucose concentration in the fermentation medium was 20 g/L. Three staged methods were used to maintain D. O. levels at 10% air saturation during each fermentor run. With the airflow at an initial setting of 0.06 L/L/min, D. O. concentration was maintained by increasing impeller speed from its initial set point of 50 rpm to its preset maximum of 940 rpm. Approximately 7 h was required for the impeller speed to increase to 940 rpm. With the impeller constant at 940 rpm, the mass flow controller then maintained D. O. levels by increasing the airflow rate from 0.06 L/L/min to its preset maximum of 1.0 L/L/min over approximately 1.5 h. At constant impeller speed and constant airflow rate, D. O. levels were maintained at 10% saturation for the remainder of the fermentation by oxygen sensor-controlled glucose feeding. At the beginning of this stage, D. O. levels fell below 10% air saturation due to residual initial glucose in the medium. This lasted for approximately 50 min before glucose (60% w/v) feeding started. The PID control parameters were set to 0.0 (off) for the derivative control ($T_D$) and 999.9 s (minimum control action) for integral control ($T_I$). $X_p$ was set to 950% to achieve a $K_c$ of 0.1.

Samples (6 mL) of fermentation broth were taken at 6 h intervals starting at 12 h. Isopropyl-β-D-thiogalactopyranoside (4.8 mg) was added when both the impeller speed and airflow had reached the maximum settings, and again at 12 h and every 6 h thereafter. Cell densities were determined by dilution of fermentation broth with water (1:100) followed by measurement of absorption at 600 nm ($OD_{600}$). Dry cell weight (g/L) was obtained using a conversion coefficient of 0.43 g/L/OD600. Fermentation broth was centrifuged to remove cells. Solute concentrations in cell-free broth were determined by $^1H$ NMR. Fermentation broth (30 mL) was removed at designated times for assay of myo-inositol-1-phosphate synthase activity. The final concentration of myo-inositol at 54 h was 20.9 g/L synthesized in 8.7% yield (mol/mol) from glucose.

The fermentation broth (950–1200 mL) was centrifuged at 18000 g for 35 min at 4° C. and the cells discarded. The resulting supernatant was acidified to pH 2.0 with concentrated $H_2SO_4$ and then centrifuged at 18000 g for 20 min to remove precipitated proteins. The clear yellow supernatant was neutralized with concentrated $NH_4OH$. The solution was decolorized with Darco KB-B activated carbon (10 g/L) for 4 h with agitation at 50 rpm and subsequently filtered through Whatman 2 filter paper. The filtered material was washed with an additional 200 mL of water.

The combined filtrates were applied to a column of AG1-x8 (acetate form, 5 cm×20 cm) at 4° C. and eluted with 1 L $H_2O$. The entire eluent (approximately 2.3 L) was then run through a column of Dowex 50 ($H^+$form, 5 cm×20 cm) at 4° C. and eluted with 500 mL $H_2O$. The resulting solution (approximately 2.8 L) was concentrated to 200 mL by boiling and then concentrated to dryness under reduced pressure. The resulting powder was dissolved in a minimal volume of $H_2O$, diluted with 6 volumes of MeOH, and stored at 4° C. to crystallize. Crystals were collected after a few days, washed with MeOH, allowed to air dry overnight, and dried under vacuum to yield white crystals (78% recovery based on inositol quantified in crude fermentation broth). $^1H$ NMR ($D_2O$) δ4.06 (dd, J=3, 3 Hz, 1 H), 3.61 (dd, J=10, 9 Hz, 2 H), 3.53 (ddd, J=10, 3, 1 Hz, 2 H), 3.28 (ddd, J=9, 9, 1 Hz, 1 H). $^{13}C$ NMR ($D_2O$) δ45.3, 43.4, 43.2, 42.1.

myo-2-Inosose. Angyal, S. J. et al. *Carbohydr. Res.* 76:121 (1979); Posternak, T., *Biochem. Prep.* 2:57 (1952). A solution containing sorbitol (1.0 g) and yeast extract (0.05 g) in 10 mL distilled, deionized water was autoclaved for 25 min and cooled to room temperature. After inoculation with Gluconobacter oxydans ATCC 621 the culture was incubated in an orbital shaker at 200 rpm for 24, h at 30° C. This G. oxydans culture was subsequently added to a second sterile solution containing myo-inositol (12.0 g, 66.7 mmol), D-sorbitol (0.4 g), and yeast extract (2.0 g) in 400 mL distilled, deionized water. After incubation in an orbital shaker at 200 rpm for 48 h at 30° C., cells were removed by centrifugation. The resulting culture supernatant was concentrated to 75 mL, MeOH (400 mL) added, and the solution maintained at −20° C. for 12 h. Precipitate which formed was filtered, washed with MeOH, and dried to afford myo-2-inosose as a white powder (8.17 g, 69%). A second crop of myo-2-inosose (3.09 g, 26%) was obtained after maintaining the filtrate at −20° C. for an additional 12 h. mp 188–192° C. $^1$H NMR (D$_2$O): $\delta$4.25 (d,J=10 Hz, 2 H), 3.66 (dd, J=9, 9 Hz), 3.26 (m, 2 H). $^{13}$C NMR (D$_2$O): $\delta$206.0, 94.3, 76.2, 74.5, 74.1, 74.0, 73.3, 73.2.

1,2,3,4-Tetrahydroxybenzene 1. A solution of myo-2-inosose (11.0 g, 61.2 mmol) in 310 mL of degassed 0.5 M H$_2$SO$_4$ was refluxed under Ar. After 9 h, the solution was cooled to 4° C. and then adjusted to pH 4 by addition of saturated aqueous NaHCO$_3$. Concentration of the reaction solution to 100 mL was followed by continuous liquid-liquid extraction for 18 h using t-butyl methyl ether (500 mL). Upon concentration of the organic layer to 100 mL, a precipitate formed which was filtered, washed with cold hexanes, and dried to afford 1 (4.72 g, 54%) as a tan powder. Addition of hexanes (300 mL) to the filtrate followed by filtering, washing, and drying of the resulting precipitate afforded additional 1 (1.08 g, 12%). mp 162–164° C. $^1$H NMR (d$_6$-acetone): $\delta$7.24 (s, 4 H), 6.20 (s, 2 H). $^{13}$C NMR (d$_6$-acetone): $\delta$139.7, 134.7, 106.2. Anal. Calcd for C$_6$H$_6$O$_4$: C, 50.71; H, 4.23. Found: C, 50.63; H, 4.32. HRMS (FAB) calcd for C$_6$H$_6$O$_4$ (M+H$^+$): 142.0266. Found: 142.0268.

SPECIFIC EXAMPLE 2

Chemical Synthesis of 1,2,3,4-Tetrahydroxybenzene

I. Results

Figure 4:
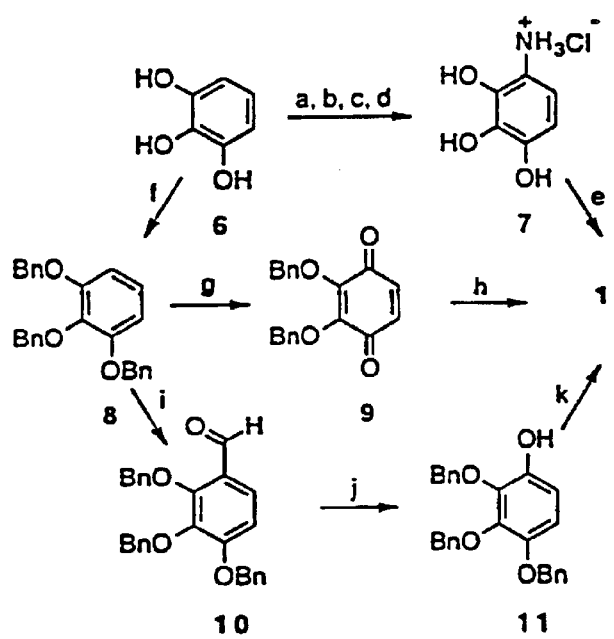
FIG. 4 is a schematic illustrating the conventional synthetic scheme for synthesizing 1,2,3,4-tetrahydroxybenzene.

Conversion of D-glucose into 1,2,3,4-tetrahydroxybenzene 1 is a three step synthesis. 1,2,3,4-Tetrahydroxybenzene 1 has historically been obtained from pyrogallol 6 by a longer route (FIG. 4) involving synthesis and subsequent hydrolysis of aminopyrogallol 7. Leston, G., In Kirk-Othmer Encyclopedia of Chemical Technology: Fourth Ed., Kroschwitz, J. I. et al. Ed., Wiley: New York, Vol. 19, p. 778 (11996); Einhorn, A. et al., Ber. 37:110 (1904). Due to the tedious nature of this synthesis (Einhorn, A. et al., Ber. 37:110 (1904)), two alternate routes (FIG. 4) were developed to obtain authentic samples of 1,2,3,4-tetrahydroxybenzene 1. Low-yielding, direct hydroxylation of protected pyrogallol 8 or higher-yielding, indirect oxidation via formyl 10 intermediacy yielded, respectively, quinone 9 and phenol 11. Hydrogenation of 9 and 11 afforded products which were identical to 1,2,3,4-tetrahydroxybenzene 1 synthesized (FIG. 2) from D-glucose.

II. Materials And Methods

General. $^1$H NMR spectra were recorded on a 300 MHz spectrometer. Chemical shifts for $^1$H NMR spectra are reported (in parts per million) relative to internal tetramethylsilane (Me$_4$Si, $\delta$=0.0 ppm) with CDCl$_3$ as solvent, to sodium 3-(trimethylsilyl)propionate-2,2,3,3-d$_4$ (TSP, $\delta$=0.0 ppm) when D$_2$O was the solvent, and to acetone (CHD$_2$COCD$_3$, $\delta$=2.04 ppm) with d$_6$-acetone. $^{13}$C NMR spectra were recorded at 75 MHz. Chemical shifts for $^{13}$C NMR spectra are reported (in parts per million) relative to CDCl$_3$ ($\delta$=77.0 ppm), relative to CD$_3$COCD$_3$ ($\delta$=29.8 ppm), and relative to internal CH$_3$OH ($\delta$=49.0 ppm) or internal CH$_3$CN ($\delta$=1.4 ppm) in D$_2$O. FAB mass spectra were performed by University of South Carolina (Columbia, S. C.). Elemental analyses were performed by Atlantic Microlab Inc. (Norcross, Ga.). Melting points were uncorrected and were determined using a Mel-Temp II melting point apparatus.

Radial chromatography was carried out with a Harrison Associates Chromatotron using 1, 2 or 4 mm layers of silica gel 60 PF$_{254}$ containing gypsum (E. Merck). Silica gel 60 (40–63 $\mu$m E. Merck) was used for flash chromatography. Analytical thin-layer chromatography (TLC) utilized precoated plates of silica gel 60 F-254 (0.25 mm, E. Merck or Whatman). TLC plates were visualized by immersion in anisaldehyde stain (by volume: 93% ethanol, 3.5% sulfuric acid, 1% acetic acid and 2.5% anisaldehyde) followed by heating. Dimethylformamide, N-methylformanilide and acetone were dried and stored over activated Linde 4Å molecular sieves under Ar. Tetrahydrofuran and diethyl ether were distilled under nitrogen from sodium benzophenone ketyl. n-Hexanes and TMEDA were distilled from sodium under Ar and stored over activated Linde 4Å molecular sieves under Ar. Organic solutions of products were dried over MgSO$_4$.

Hydrogenation of 2,3-dibenzyloxy-1,4-benzoquinone 9. A solution of 9 (0.18 9, 0.56 mmol) in EtOH (7.0 mL) was stirred with 10% Pd on C (0.050 g) at room temperature under H$_2$ (1.0 atm) for 3 h. The solution was filtered through Celite® and concentrated to afford a tan solid (0.079 g, 99%) which was identical by $^1$H and $^{13}$C NMR to 1 obtained from myo-2-inosose. Hydrogenation of 2,3,4-tribenzyloxyphenol 11. A solution of 11 (5.8 g, 14.1 mmol) in EtOH (100 mL) was stirred with 10% Pd on C (1.0 g) at room temperature under H$_2$ (1.0 atm) for 2 h. The solution was filtered through Celite® and concentrated. The residue was purified by flash chromatography (MeOH/CH$_2$Cl$_2$, 1:9, v/v) affording a product which was identical by $^1$H and $^{13}$C NMR to 1 obtained from myo-2-inosose.

1,2,3-Tribenzyloxybenzene 8. Lowe, W. et al., Arch. Pharm. (Weinheim) 327:255 (1994). Benzyl bromide (57 mL, 0.481 mol) and then K$_2$CO$_3$ (100 g, 0.725 mol) were added to a solution of pyrogallol (20 g, 0.1 59 mol) in 200 mL dry, degassed acetone under Ar. This reaction mixture was subsequently stirred for 30 min at room temperature and then for 24 h at reflux under Ar. A solution of NaOH (1.6 g) in MeOH (32 mL) was then added and the reaction refluxed for an additional 30 min. After cooling to room temperature, solids were filtered and washed with acetone. The filtrate was concentrated and the residue recrystallized from MeOH to afford 8 (52 g, 83%) as an off-white solid. mp 67–68° C. $^1$H NMR (CDCl$_3$): $\delta$7.44–7.19 (m, 15 H), 6.85 (dd, J=9, 9 Hz, 1 H), 6.57 (d, J=8.2 Hz, 2 H), 5.05 (s, 2 H), 5.02 (s, 4 H). $^{13}$C NMR (CDCl$_3$): $\delta$152.9, 138.4, 137.8, 137.0, 128.4, 128.3, 128.0, 127.8, 127.6 (2), 127.3, 127.2, 123.5, 107.7, 75.0, 70.9.

2,3-Dibenzyloxy-1,4-benzoquinone 9. To a solution of 1,2,3-tribenzyloxybenzene 8 (2.0 g, 5.0 mmol) in HOAc (30 mL), K$_3$Fe(CN)$_6$ (0.82 g, 2.5 mmol) and 30% H$_2$O$_2$ (1.3 g, 11.5 mmol) were added and the resulting solution stirred at room temperature for 18 h. The solution was diluted with 50 mL CH$_2$Cl$_2$ and the organic layer subsequently washed with H$_2$O, saturated aqueous NaHCO$_3$ and brine. Drying and concentration resulted in a red oil. Purification by radial chromatography (2 mm thickness, EtOAc/hexane, 1:19, v/v)

afforded 9 as a red oil. $^{1}$H NMR (CDCl$_3$): δ7.36–7.32 (m, 10 H), 6.58 (s, 2 H), 5.20 (s, 4 H). $^{13}$C NMR (CDCl$_3$): δ184.1, 145.2, 136.1, 134.6 128.5, 128.4, 128.1, 75.1. Anal. Calcd for C$_{20}$H$_{18}$O$_4$: C, 74.99; H, 5.03. Found: C, 75.04; H, 5.06. HRMS (FAB) calcd for C$_{20}$H$_{16}$O$_4$ (M+H$^+$): 320.1049. Found: 320.1059.

2,3,4-Tribenzyloxybenzaldehyde 10. Kolonits, P. et al., *Acta Chim. Hung.* 113:367 (1983). POCl$_3$ (155 mL, 1.66 mol) was slowly added to N-methylformanilide (175 mL, 1.4 mol) at room temperature under Ar which resulted in formation of a yellow solid. After 2 h, the solid was treated with a solution of 1,2,3-tribenzyloxybenzene 8 (20 g, 51 mmol) in anhydrous DMF (40 mL) and heated to 60° C. After 3 h, the resulting crimson solution was cooled to room temperature and then poured into ice water (3 L) with vigorous stirring for 12 h. The resulting brown precipitate was filtered, washed with hexanes (3×100 mL) and finally recrystallized from MeOH to afford 10 (19.8 g, 93%) as a white powder. mp 73–74° C. $^{1}$H NMR (CDCl$_3$): δ10.11 (s, 1 H), 7.57 (d, J=9 Hz, 1 H), 7.44–7.28 (m, 15 H), 6.83 (d, J=9 Hz, 1 H), 5.21(s, 2 H), 5.16 (s, 2 H), 5.08 (s, 2 H); $^{13}$C NMR (CDCl$_3$): δ188.8, 158.5, 155.9, 141.1, 136.9, 136.2, 135.8, 128.6, 128.5 (2), 128.3 (2) 128.2, 127.5, 124.0, 109.1, 76.8, 75.5, 70.9. Anal. Calcd for C$_{28}$H$_{24}$O$_4$: C, 79.22; H, 5.70. Found: C, 79.17; H, 5.80. HRMS (FAB) calcd for C$_{28}$H$_{24}$O$_4$ (M+H$^+$): 424.1675. Found: 424.1669.

2,3,4-Tribenzyloxyphenol 11. Kolonits, P. et al., *Acta Chim Hung.* 113:367 (1983). A solution of 30% H$_2$O$_2$ (6 mL, 57.8 mmol) and 85% formic acid (32 mL, 600 mmol) was added dropwise to a solution of 2,3,4-tribenzyloxybenzaldehyde 10 (9.8 g, 23.1 mmol) in CH$_2$Cl$_2$ (50 mL) over 30 min at 0° C. After 1 h of stirring at 0° C., the reaction was stirred at room temperature for 24 h. The reaction was subsequently cooled to 4° C. and diluted with 10% (w/v) aqueous Na$_2$SO$_3$ (50 mL). The aqueous phase was washed with CH$_2$Cl$_2$ (3×40 mL). Drying and: concentration afforded a brown oil which was dissolved in a methanolic solution of NaOMe (30 mL, 0.1 N) and refluxed. After 10 min, the solution was cooled to 4° C. and acidified with 6 N HCl. MeOH was removed in vacuo. The mixture was diluted with H$_2$O (15 mL) followed by extraction of the aqueous phase with benzene (3×40 mL). Drying and concentration afforded 11 (9.0 g, 95%) as a brown oil. $^{1}$H NMR (CDCl$_3$): δ7.45–7.31 (m, 15 H), 6.65 (d, J=9 Hz, 1 H), 6.58 (d, J=9 Hz, 1 H), 5.28 (s, 1 H), 5.12 (s, 2 H), 5.11 (s, 2 H), 5.04 (s, 2 H). $^{13}$C NMR (CDCl$_3$): δ146.0, 144.0, 142.0, 139.6, 137.3, 137.1, 136.8, 128.4, 128.3 (2), 128.2, 127.9, 127.7, 127.4, 110.4, 109.0, 75.6, 75.3, 71.7. Anal. Calcd for C$_{27}$H$_{24}$O$_4$: C, 78.62; H, 5.87. Found: C, 78.71; H, 5.86. HRMS (FAB) calcd for. C$_{27}$H$_{24}$O$_4$ (M+H$^+$): 412.1675. Found: 412.1673.

SPECIFIC EXAMPLE 3

Synthesis of Coenzyme Q from 1.2,3,4-Tetrahydroxybenzene

I. Results

Figure 5:
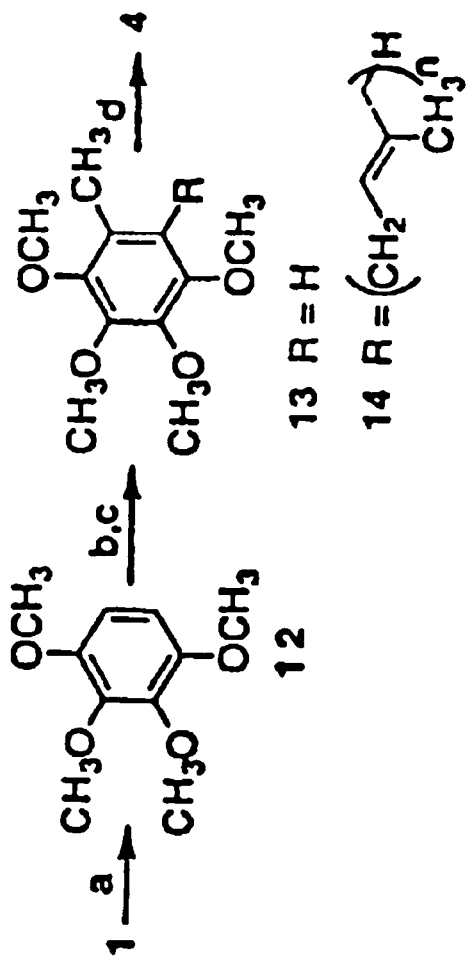
FIG. 5 is a schematic illustrating the synthesis scheme for converting 1,2,3,4-tetrahydroxybenzene to Coenzyme Q.

Variations in strategies employed for hydroxyl protection combined with the ease of metallation and alkylation of the aromatic nucleus makes 1 a versatile intermediate for the synthesis of a wide spectrum of naturally-occurring 1,2,3,4-tetrahydroxybenzene derivatives. For example, permethylation (FIG. 5) of 1 leads to tetramethyl 12 which undergoes facile lithiation and methylation affording 13 in high yield. Formation of an organocuprate from 13, farnesylation, and subsequent reaction with (NH$_4$)$_2$Ce(NO$_3$)$_6$ affords coenzyme Q$_{n=3}$4. This four-step synthesis of coenzyme Q$_n$ from tetrahydroxybenzene 1 is equal in length to the shortest reported (Keinan, E. et al., *J. Org. Chem.* 52:3872 (1987)) synthesis of coenzyme Q$_n$ which uses p-cresol as a starting material and substantially shorter than syntheses of coenzyme Q$_n$ from pyrogallol, gallic acid, or vanillin. Syper, L. et al., *Tetrahedron* 36:123 (1980); Sugihara, H. et al., *Liebigs Ann. Chem.* 763:109 (1972); Mayer, J. et al., *Meth. Enzymol.* 18:182 (1971).

Only one oxygen atom in coenzyme Q$_n$, a shikimate pathway product, is directly derived from D-glucose. The remaining oxygen atoms are derived from O$_2$ via enzyme-catalyzed hydroxylations. Trihydroxybenzenes, pyrogallol, and phloroglucinol possess the maximum number of oxygen atoms attached to a benzene nucleus by the shikimate pathway or polyketide biosynthesis in lieu of enzyme-catalyzed hydroxylation. At least a dozen enzymes are required to disassemble and reassemble the carbon atoms of D-glucose into the benzene nucleus of coenzyme Q$_n$, pyrogallols, and phloroglucinols. By comparison, synthesis of 1,2,3,4-tetrahydroxybenzene 1 via myo-inositol intermediacy requires only four enzymes and an acid-catalyzed dehydration for all six carbon and all four oxygen atoms to be directly derived from the carbon and oxygen atoms of D-glucose. The method of the present invention for synthesis of 1,2,3,4-tetrahydroxybenzene 1 is thus a useful example of enzyme and atom (Trost, B. M., *In Green Chemistry*, Anastas, P. T., Williamson, T. C. Eds., Oxford: New York, Chap. 6 (1 998)) economy in organic synthesis in addition to being a significant strategic departure from previous biocatalytic syntheses of aromatic chemicals from D-glucose.

II. Materials And Methods

General. $^{1}$H NMR spectra were recorded on a 300 MHz spectrometer. Chemical shifts for $^{1}$H NMR spectra are reported (in parts per million) relative to internal tetramethylsilane (Me$_4$Si, δ=0.0 ppm) with CDCl$_3$ as solvent, to sodium 3-(trimethylsilyl)propionate-2,2,3,3-d$_4$ (TSP, δ=0.0 ppm) when D$_2$O was the solvent, and to acetone (CHD$_2$COCD$_3$, δ=2.04 ppm) with d$_6$-acetone. $^{13}$C NMR spectra were recorded at 75 MHz. Chemical shifts for $^{13}$C NMR spectra are reported (in parts per million) relative to CDCl$_3$ (δ=77.0 ppm), relative to CD$_3$COCD$_3$ (δ=29.8 ppm), and relative to internal CH$_3$OH (δ=49.0 ppm) or internal CH$_3$CN (δ=1.4 ppm) in D$_2$O. FAB mass spectra were performed by University of South Carolina (Columbia, S.C.). Elemental analyses were performed by Atlantic Microlab Inc. (Norcross, Ga.). Melting points were uncorrected and were determined using a Mel-Temp II melting point apparatus.

Radial chromatography was carried out with a Harrison Associates Chromatotron using 1, 2 or 4 mm layers of silica gel 60 PF$_{254}$ containing gypsum (E. Merck). Silica gel 60(140–63 μm E. Merck) was used for flash chromatography. Analytical thin-layer chromatography (TLC) utilized precoated plates of silica gel 60 F-254 (0.25 mm, E. Merck or Whatman). TLC plates were visualized by immersion in anisaldehyde stain (by volume: 93% ethanol, 3.5% sulfuric acid, 1% acetic acid and 2.5% anisaldehyde) followed by heating. Dimethylformamide, N-methylformanilide and acetone were dried and stored over activated Linde 4Å molecular sieves under Ar. Tetrahydrofuran and diethyl ether were distilled under nitrogen from sodium benzophenone ketyl. n-Hexanes and TMEDA were distilled from sodium under Ar and stored over activated Linde 4Å molecular sieves under Ar. Organic solutions of products were dried over MgSO$_4$.

1,2,3,4-Tetramethoxybenzene 12. Syper, L. et al., Tetrahedron 36:123 (19801. A solution of 1,2,3,4- tetrahydroxybenzene 1 (8.4 g, 59 mmol) and dimethyl sulfate (37.5 mL, 0.396 mol) in EtOH (21 mL) was added dropwise to an 8.5 M aqueous solution of NaOH (42 mL) over 20 min at room temperature. After. 2 h, the reaction was diluted with $H_2O$ (300) mL and cooled to $-20°$ C. for 12 h. The resulting precipitate was filtered, washed with $H_2O$, and then recrystallized from hexanes to afford 12 (8.12 g, 69%) as colorless needles. mp 84–85° C. $^1H$ NMR ($CDCl_3$): δ6.58 (s, 2 H), 3.90 (s, 6 H) 3.82 (s, 6 H). $^{13}C$ NMR ($CDCl_3$): δ147.7, 143.3, 106.3, 61.1, 56.3. Anal. Calcd for $C_{10}H_{14}O_4$: C, 60.59; H, 7.12. Found: C, 60.44; H, 7.07.

2,3,4,5-Tetramethoxytoluene 13. Syper, L. et al., *Tetrahedron* 36:123 (1980). To a solution of 1,2,3,4-tetramethoxybenzene 12 (4.0 g, 20.2 mmol) and TMEDA (6 mL, 38.0 mmol) in hexanes (44 mL) and THF (80 mL) at 0° C. under Ar, n-BuLi in hexane (1.6 M, 25.6 mmol) was added dropwise over a 10 min period and the reaction stirred for 30 min at 0° C. under Ar. Subsequent to dropwise addition of $CH_3I$ (20 mL, 160 mmol) over an 8 min period, the reaction was stirred for 3 h at 0° C. under Ar and then quenched by addition of aqueous $NH_4Cl$ and ether (20 mL). The organic layer was sequentially washed with concentrated $NH_4OH$, water, and brine. Drying and concentration of the organic layer was followed by purification of the residue by flash chromatography (hexanes, hexanes/EtOAc, 19:1, v/v) to afford 13 as a clear oil (3.6 g, 83%). $^1H$ NMR ($CDCl_3$): δ6.45 (s, 1 H), 3.93 (s, 3 H), 3.87 (s, 3 H), 3.82 (s, 3 H), 3.79 (s, 3 H), 2.23 (s, 3 H). $^{13}C$ NMR ($CDCl_3$): δ149.0, 146.9, 145.3, 140.7, 125.7, 108.2, 61.0, 60.9, 60.5, 55.9, 15.7.

Protected coenzyme $O_3$ 14. Keinan, E. et al., *J. Org. Chem.* 52:3872 (1987). n-BuLi (1.6 M, 0.9 mL) was added dropwise over a 15 min period to a solution of 1,2,3,4-tetramethoxytoluene 13(0.212 g, 1 mmol) and TMEDA (0.3 mL, 1.9 mmol) in hexane (2.2 mL) at 0° C. under Ar. This yellow precipitate-containing reaction mixture was then stirred at 0° C. under Ar for 30 min, diluted with THF (4 mL) and ether (11 mL), followed by addition of CuCN (0.125 g, 1.4 mmol). After stirring for 30 min at 0° C. under Ar, the temperature was reduced to $-78°$ C., and a solution of farnesyl bromide (0.285 g, 1 mmol) in hexane (2 mL) was dropwise added over a 30 min period. Further reaction for 3 h at $-78°$ C. and subsequent slow warming to room temperature was followed by addition of saturated aqueous $NH_4Cl$ (10 mL) and ether (20 mL). Washing the organic phase with concentrated $NH_4OH$, water, and brine was followed by drying and concentration. Purification of the residue by radial chromatography (2 mm thickness, hexane/EtOAc, 9:1, v/v) afforded 14 as a clear oil (0.236 g, 57%). $^1H$ NMR ($CDCl_3$): δ5.12–5.01 (m, 3 H), 3.90 (s, 6 H), 3.78 (s, 6 H), 3.32 (d, J=7 Hz, 2 H), 2.14 (s, 3 H), 2.08–1.91 (m, 8 H), 1.77 (s, 3 H), 1.66 (s, 3 H), 1.58 (s, 6 H). $^{13}C$ NMR ($CDCl_3$): δ147.8, 147.6, 144.9, 144.6, 135.0, 134.9, 131.2, 129.2, 125.4, 124.3, 124.1, 122.8, 61.1, 60.6, 39.7, 26.7, 26.5, 25.7, 25.6, 17.6, 16.2, 15.9, 11.7.

Coenzyme $Q_3$ 4. Keinan, E. et al., *J. Org. Chem.* 52:3872 (1987). A suspension maintained at 0° C. resulting from addition of pyridine-2,6-dicarboxylate (0.125 9, 0.75 mmol) to a solution of protected coenzyme $Q_3$ 14 in $CH_3CN$ (1.4 mL) and water (0.6 mL) at 0° C. was reacted with a 0° C. solution of $(NH_4)_2Ce(NO_3)_6$ (0.411 g, 0.75 mmol) in $CH_3CN$ (0.4 mL) and water (0.4 mL) added dropwise over a 10 min period. After 40 min at 0° C., the reaction was warmed to room temperature and stirred for 20 min. Water (10 mL) was added to the reaction mixture and the resulting solution extracted with $CH_2Cl_2$ (3×100 mL). The combined organic phases were dried, concentrated, and purified by radial chromatography (1 mm thickness, hexane/EtOAc, 19:1, v/v) to afford 4 (0.053 g, 46%) as an orange oil. $^1H$ NMR ($CDCl_3$): δ5.07 (dd, J=7, 7 Hz, 1 H), 5.05 (dd, J=7, 7 Hz, 1 H), 4.94 (dd, J=7, 7 Hz, 1 H), 3.99 (s, 3 H), 3.98 (s, 3 H), 3.18 (d, J=6.8 Hz, 2 H), 2.08–1.91 (m, 8 H), 2.01 (s, 3 H), 1.74 (s, 3 H), 1.67 (s, 3 H), 1.59.(s, 3 H), 1.58 (s, 3 H); $^{13}C$ NMR ($CDCl_3$): δ_184.7, 183.9, 144.3, 144.2, 141.6, 138.8, 137.6, 135.2, 131.3, 124.3, 123.8, 118.8, 61.1, 39.7, 26.7, 26.4, 25.7, 25.3, 17.6, 16.3, 16.0, 11.9; HRMS (FAB) calcd for $C_{24}H_{34}O_4$ ($M+H^+$): 386.2457. Found: 386.2461

SPECIFIC EXAMPLE 4

Synthesis of Myo-2-Inosose by a Single Microbe

Myo-2-inosose (1 g/L), myo-inositol (18 g/L), and myo-inositol-1-phosphate (3.1 g/L) were synthesized by *E. coli* JWF1/pAD2.28 A in 9.6% (mol/mol) yield from glucose under fed-batch fermentation conditions as described in Specific Example 1. The fermentation ran for 54 h with incremental addition of IPTG (0.0048 g added each time) at 7 h, 12 h, 18 h, 24 h, 30 h, 36 h, 42 h, 48 h, and 54 h. The myo-2-inosose can then be converted to 1,2,3,4-tetrahydroxybenzene by acid-catalyzed dehydration as described in Specific Example 1.

Plasmid pAD2.28 A carries INO1 under $P_{lac}$ promoter control, iolG under $P_{lac}$ promoter control, $lac^Q$, and serA. INO1 encodes myo-inositol-1-phosphate synthase and was cloned out of *Saccharomyces cerevisiae*. Inositol dehydrogenase is encoded by the iolG locus, which was cloned out of *Bacillus subtilis*.

SPECIFIC EXAMPLE 5

Conversion of 1,2,3,4-Tetrahydroxybenzene to Pyrogallol

A solution consisting of 0.4 g of NaOH (10 mmol) dissolved in 10 mL $H_2O$ was freeze-thaw degassed three times under Ar. This solution was then added via cannula under Ar to a 250 mL Parr bottle containing 1,2,3,4-tetrahydroxybenzene (1.42 g, 10 mmol) and 5% $Rh/Al_2O_3$ (0.25 g), which had been flushed with Ar and then sealed with a septum. The resulting red/brown solution was hydrogenated under 50 psi. $H_2$ using a Parr Hydrogenator. After 12 h, the solution was filtered through Celite® and the catalyst rinsed with 10 mL $H_2O$. The resulting dark brown solution was adjusted to pH=6.0 with 10% HCl and then concentrated to a brown oil. The oil was dissolved in 50 mL 0.5 M $H_2SO_4$ that had been degassed by aeration with Ar for 20 minutes. The solution was heated to reflux under Ar for 12 h, cooled to room temperature, and then extracted with $Et_2O$ (4×50 mL). The combined organic layers were dried over $MgSO_4$, filtered and concentrated to a brown oil. Kugel-Rohr distillation of the oil under vacuum (1 mm Hg) at 90° C. afforded 0.56 g pyrogallol (4.44 mmol, 44% yield) as a white, crystalline solid.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are incorporated by reference as if fully set forth.

We claim:

1. A method for the production of 1,2,3,4-tetrahydroxybenzene, comprising:
   a) incubating, in the presence of a carbon source, a first microbe comprising a recombinant DNA encoding a naturally occurring myo-inositol-1-phosphate synthase and a second microbe which expresses a naturally occurring inositol dehydrogenase to produce myo-2-inosose; and
   b) converting the myo-2-inosose to 1,2,3,4-tetrahydroxybenzene by acid catalyzed dehydration.

2. The method of claim 1 wherein the first microbe comprises an INO1 gene.

3. The method of claim 2 wherein the INO1 gene comprises a *Saccharomyces cerevisiae* INO1 gene.

4. The method of claim 3 wherein the INO1 gene is comprised by pAD1.88A.

5. The method of claim 1 wherein the first microbe is an *Escherichia coli*.

6. The method of claim 5 wherein the *Escherichia coli* is JWF1/pAD1.88A.

7. The method of claim 1 wherein the second microbe is *Gluconobacter oxydans*.

8. The method of claim 7 wherein the *Gluconobacter oxydans* is ATCC 621.

9. The method of claim 1 wherein the second microbe comprises a recombinant DNA encoding the naturally occurring inositol dehydrogenase.

10. The method of claim 9 wherein the DNA encoding the naturally occurring inositol dehydrogenase comprises a *Bacillus subtilis* iolG gene.

11. The method of claim 1 wherein the carbon source comprises glucose.

12. A method for the production of 1,2,3-trihydroxybenzene, comprising producing 1,2,3,4-tetrahydroxybenzene in accordance with claim 1 and reducing the 1,2,3,4-tetrahydroxybenzene to 1,2,3-trihydroxybenzene.

13. A microbe comprising a recombinant DNA encoding myo-inositol-1-phosphate synthase.

14. The microbe of claim 13 wherein the recombinant DNA encoding myo-inositol-1-phosphate synthase comprises an INO1 gene.

15. The microbe of claim 14 wherein the INO1 gene comprises a *Saccharomyces cerevisiae* INO1 gene.

16. The microbe of claim 15 wherein the INO1 gene is comprised by pAD1.88A.

17. The microbe of claim 13 which is an *Escherichia coli*.

18. A fermentation composition comprising a first microbe which comprises a recombinant DNA encoding a naturally occurring myo-inositol-1-phosphate synthase and a second microbe which expresses a naturally occurring inositol dehydrogenase.

19. The fermentation composition of claim 18 wherein the first microbe comprises an INO1 gene.

20. The fermentation composition of claim 19 wherein the INO1 gene comprises a *Saccharomyces cerevisiae* INO1 gene.

21. The fermentation composition of claim 20 wherein the INO1 gene is comprised by pAD1.88A.

22. The fermentation composition of claim 18 wherein the first microbe is an *Escherichia coli*.

23. The fermentation composition of claim 22 wherein the *Escherichia coli* is JWF1/pAD1.88A.

24. The fermentation composition of claim 18 wherein the second microbe is *Gluconobacter oxydans*.

25. The fermentation composition of claim 24 wherein the *Gluconobacter oxydans* is ATCC 621.

26. The fermentation composition of claim 18 wherein the second microbe comprises a recombinant DNA encoding the naturally occurring inositol dehydrogenase.

27. The fermentation composition of claim 26 wherein the DNA encoding the naturally occurring inositol dehydrogenase comprises a *Bacillus subtilis* iolG gene.

28. The fermentation composition of claim 18 further comprising glucose.

29. A method for the production of 1,2,34-tetrahydroxybenzene, comprising:
   a) incubating, in the presence of a carbon source, a first microbe comprising a recombinant DNA encoding a naturally occurring myo-inositol-1-phosphate synthase, thereby forming myo-inositol;
   b) incubating the myo-inositol in the presence of a second microbe which expresses inositol dehydrogenase activity, thereby forming myo-2-inosose; and
   c) converting the myo-2-inosose to 1,2,3,4-tetrahydroxybenzene by acid catalyzed dehydration.

30. The method of claim 29 wherein the first microbe comprises an INO1 gene.

31. The method of claim 30 wherein the INO1 gene comprises a *Saccharomyces cerevisiae* INO1 gene.

32. The method of claim 31 wherein the INO1 gene is comprised by pAD1.88A.

33. The method of claim 29 wherein the first microbe is an *Escherichia coli*.

34. The method of claim 33 wherein the *Escherichia coli* is JWF1/pAD1.88A.

35. The method of claim 29 wherein the second microbe is *Gluconobacter oxydans*.

36. The method of claim 35 wherein the *Gluconobacter oxydans* is ATCC 621.

37. The method of claim 29 wherein the second microbe comprises a recombinant DNA encoding inositol dehydrogenase.

38. The method of claim 37 wherein the DNA encoding inositol dehydrogenase comprises a *Bacillus subtilis* iolG gene.

39. The method of claim 29 wherein the carbon source comprises glucose.

40. A method for the production of 1,2,3-trihydroxybenzene, comprising producing 1,2,3,4-tetrahydroxybenzene in accordance with claim 29 and reducing the 1,2,3,4-tetrahydroxybenzene to 1,2,3-trihydroxybenzene.

41. A microbe comprising a recombinant DNA encoding myo-inositol-1-phosphate synthase, wherein the microbe is *Escherichia coli* JWF1/pAD1.88A.

* * * * *

UNITED STATES PATENT AND TRADEMARK OFFICE
CERTIFICATE OF CORRECTION

PATENT NO.      : 6,750,049 B1
DATED           : June 15, 2004
INVENTOR(S)     : John W. Frost and Chad A. Hansen It is certified that error appears in the above-identified patent and that said Letters Patent is hereby corrected as shown below:

Column 1,
Line 28, "(1953):" should be -- (1953); --.
Line 34, "(1991)" should be -- (1991); --.
Line 37, "(1988):" should be -- (1988); --.

Column 4,
Line 53, "(11990)" should be -- (1990) --.

Column 7,
Line 20, "11989))" should be -- (1989)) --.

Column 8,
Line 44, "NH,Cl" should be -- $NH_4Cl$ --.

Column 9,
Lines 10 and 15, "lacl$^Q$" should be -- lacl$^q$ --.
Line 38, "(15x25 cm)" should be -- (5x25 cm) --.
Line 52, "11996))" should be -- (1996)) --.

Column 10,
Line 33, "g/L/OD600" should be -- $g/L/OD_{600}$ --.

Column 11,
Line 5, "24, h" should be -- 24 h --.
Line 49, "(11996)" should be -- (1996) --.
Line 67, "$_{\delta=}2.04$" should be -- $\delta = 2.04$ --.

Column 12,
Line 29, "(0.18 9," should be -- (0.18 g, --.
Line 45, "0.1 59" should be -- 0.159 --.

Column 13,
Line 2, "($CDCl_{3)}$: $_\delta$ 184.1" should be -- ($CDCl_3$: $\delta$ 184.1 --.
Line 4, "$H_{18}$" should be -- $H_{16}$ --.
Line 36, "and:" should be -- and --.
Line 54, "1.2,3,4" should be -- 1,2,3,4 --.

Column 14,
Line 27, "(1 998))" should be -- (1998)) --.
Line 52, "(140" should be -- (40 --.
Line 67, "(19801." should be -- (1980). --.

UNITED STATES PATENT AND TRADEMARK OFFICE
CERTIFICATE OF CORRECTION

PATENT NO. : 6,750,049 B1
DATED : June 15, 2004
INVENTOR(S) : John W. Frost and Chad A. Hansen It is certified that error appears in the above-identified patent and that said Letters Patent is hereby corrected as shown below:

Column 15,
Line 33, "$O_3$" should be -- $Q_3$ --.
Line 63, "(0.125 9," should be -- (0.125 g, --.

Column 16,
Line 32, "$P_{lac}$" Should be -- $P_{tac}$ --.
Line 33, "$lac^Q$" should be -- $lacI^q$ --.

Column 17,
Lines 54-55, delete "The microbe of claim 15 wherein the INO1 gene is comprised by pAD1.88A." and insert -- A microbe comprising a recombinant DNA encoding myo-inositol-1-phosphate synthase, wherein the recombinant DNA is plasmid pAD1.88A. --.

Column 18,
Line 21, "1,2,34" should be -- 1,2,3,4 --.
Line 28, after "expresses" insert -- a naturally occurring --.
Line 29, after "dehydrogenase" delete "activity".
Lines 47 and 49, after "encoding" insert -- the naturally occurring --.

Signed and Sealed this

Fifteenth Day of November, 2005

JON W. DUDAS
*Director of the United States Patent and Trademark Office*